US00PP21234P2

(12) United States Plant Patent
Larsen

(10) Patent No.: US PP21,234 P2
(45) Date of Patent: Aug. 24, 2010

(54) ***OSTEOSPERMUM* PLANT NAMED 'SUNPIX0805'**

(50) Latin Name: *Osteospermum ecklonis*
Varietal Denomination: Sunpix0805

(75) Inventor: Bjarne Nyholm Larsen, Odense (DK)

(73) Assignee: Sunny Gronnegyden APS, Odense (DK)

( * ) Notice: Subject to any disclaimer, the term of this patent is extended or adjusted under 35 U.S.C. 154(b) by 0 days.

(21) Appl. No.: 12/386,339

(22) Filed: Apr. 15, 2009

(51) Int. Cl.
*A01H 5/00* (2006.01)

(52) U.S. Cl. ..... Plt./360

(58) Field of Classification Search ..... Plt./360
See application file for complete search history.

*Primary Examiner*—Annette H Para
(74) *Attorney, Agent, or Firm*—C.A. Whealy

(57) ABSTRACT

A new and distinct cultivar of *Osteospermum* plant named 'Sunpix0805', characterized by its compact and mounded plant habit; freely branching growth habit; freely flowering habit; daisy-type inflorescences with bright yellow-colored ray florets; and good garden performance.

2 Drawing Sheets

Botanical designation: *Osteospermum ecklonis.*
Cultivar denomination: 'Sunpix0805'.

BACKGROUND OF THE INVENTION

The present invention relates to a new and distinct cultivar of *Osteospermum* plant, botanically known as *Osteospermum ecklonis*, and hereinafter referred to by the name 'Sunpix0805'.

The new *Osteospermum* plant is a product of a planned breeding program conducted by the Inventor in Odense, Denmark. The objective of the program is to create and develop new *Osteospermum* cultivars with uniformly mounded plant habit, freely flowering habit and attractive inflorescence coloration.

The new *Osteospermum* plant originated from a cross-pollination by the Inventor in May, 2006 of a proprietary selection of *Osteospermum ecklonis* identified as code number 00.90.019, not patented, as the female, or seed parent with the *Osteospermum ecklonis* 'Sunny Serena', disclosed in U.S. Plant Pat. No. 15,693, as the male, or pollen, parent. The new *Osteospermum* was discovered and selected by the Inventor as a single flowering plant within the progeny of the stated cross-pollination in a controlled greenhouse environment in Odense, Denmark in May, 2007.

Asexual reproduction of the new *Osteospermum* plant by terminal cuttings in a controlled greenhouse environment in Odense, Denmark since November, 2007, has shown that the unique features of this new *Osteospermum* plant are stable and reproduced true to type in successive generations.

SUMMARY OF THE INVENTION

Plants of the new *Osteospermum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunpix0805'. These characteristics in combination distinguish 'Sunpix0805' as a new and distinct cultivar of *Osteospermum:*

1. Compact and mounded plant habit.
2. Freely branching growth habit.
3. Freely flowering habit.
4. Daisy-type inflorescences with bright yellow-colored ray florets.
5. Good garden performance.

Plants of the new *Osteospermum* differ from plants of the female parent selection in the following characteristics:

1. Plants of the new *Osteospermum* are more compact and more freely branching than plants of the female parent selection.
2. Plants of the new *Osteospermum* have smaller leaves than plants of the female parent selection.
3. Plants of the new *Osteospermum* have smaller inflorescences than plants of the female parent selection.

Plants of the new *Osteospermum* differ from plants of the male parent, 'Sunny Serena' in the following characteristics:

1. Plants of the new *Osteospermum* are more compact than and not as vigorous as plants of 'Sunny Serena'.
2. Plants of the new *Osteospermum* have smaller leaves and inflorescences than plants of 'Sunny Serena'.
3. Plants of the new *Osteospermum* and 'Sunny Serena' differ in ray floret color as plants of 'Sunny Serena' have pale yellow-colored ray florets.

Plants of the new *Osteospermum* can be compared to plants of *Osteospermum ecklonis* 'Sunny Alex', not patented. In side-by-side comparisons conducted in Odense, Denmark, plants of the new *Osteospermum* differed from plants of 'Sunny Alex' in the following characteristics:

1. Plants of the new *Osteospermum* were more compact than plants of 'Sunny Alex'.
2. Plants of the new *Osteospermum* were less vigorous than plants of 'Sunny Alex'.

BRIEF DESCRIPTION OF THE PHOTOGRAPHS

The accompanying photographs illustrate the overall appearance of the new *Osteospermum*. These photographs shows the colors as true as it is reasonably possible to obtain in colored reproductions of this type.

Colors in the photographs may differ slightly from the color values cited in the detailed botanical description which accurately describe the colors of the new *Osteospermum*.

The photograph on the first sheet comprises a side perspective view of a typical flowering plant of 'Sunpix0805'.

The photograph on the second sheet is a close-up view of typical inflorescences of 'Sunpix0805'.

DETAILED BOTANICAL DESCRIPTION

The aforementioned photographs, following observations and measurements describe plants grown in Bonsall, Calif. during the spring in a polyethylene-covered greenhouse and under conditions and practices which approximate those generally used in commercial *Osteospermum* production. During the production of the plants, day temperatures averaged 24° C. and night temperatures averaged 14° C. Plants were pinched one time. Plants were 16 weeks old when the photographs and description were taken. In the following description, color references are made to The Royal Horticultural Society Colour Chart, 2001 Edition, except where general terms of ordinary dictionary significance are used.

Botanical classification: *Osteospermum ecklonis* 'Sunpix0805'.

Parentage:

*Female, or seed, parent.*—Proprietary selection of *Osteospermum ecklonis* identified as code number 00.90.019, not patented.

*Male, or pollen, parent.*—*Osteospermum ecklonis* 'Sunny Serena', disclosed in U.S. Plant Pat. No. 15,693.

Propagation:

*Type.*—Terminal vegetative cuttings.

*Time to initiate roots, summer.*—About ten days at 18° C.

*Time to initiate roots, winter.*—About twelve days at 18° C. to 20° C.

*Time to produce a rooted cutting, summer.*—About three weeks at 18° C. to 20° C.

*Time to produce a rooted cutting, winter.*—About four weeks at 18° C.

*Root description.*—Medium in thickness, fibrous; light tan in color.

*Rooting habit.*—Freely branching; moderately dense.

Plant description:

*Plant form/growth habit.*—Compact, upright and mounded plant habit.

*Plant height.*—About 24 cm.

*Plant diameter.*—About 32 cm.

*Lateral branch length.*—About 11 cm.

*Foliage description.*—Arrangement/quantity: Alternate, simple; leaves sessile; about 17 leaves per lateral branch. Length: About 4.7 cm. Width: About 1.2 cm. Shape: Narrowly oblanceolate. Apex: Abruptly acuminate. Base: Narrowly cuneate. Margin: Entire with infrequent deep indentations. Texture, upper and lower surface: Slightly pubescent. Color: Developing leaves, upper surface: Close to 137A. Developing leaves, lower surface: Close to 138B. Fully expanded leaves, upper surface: Close to 137C; venation, close to 144B. Fully expanded leaves, lower surface: Close to 137A; venation, close to 143C.

Inflorescence description:

*Appearance.*—Daisy-type inflorescences; inflorescences positioned above and beyond the foliage; inflorescences terminal and axillary. Disc and ray florets developing acropetally on a capitulum. Freely flowering habit; about nine inflorescences developing per lateral branch.

*Fragrance.*—Moderately fragrant; musky.

*Flowering response.*—Plants of the new *Osteospermum* flower continuously from February to September; inflorescences last about two to three weeks on the plant; inflorescences persistent.

*Inflorescence bud.*—Height: About 1.1 cm. Diameter: About 9 mm. Shape: Spherical. Color: Close to 143B.

*Inflorescence size.*—Diameter: About 5 cm. Depth (height): About 1.8 cm. Disc diameter: About 1.1 cm. Receptacle diameter: About 8 mm. Receptacle height: About 3 mm.

*Ray florets.*—Length: About 2.9 cm. Width: About 3 mm. Shape: Narrowly oblanceolate. Apex: Obtuse with shallow lobes. Margin: Entire. Texture, upper and lower surfaces: Smooth, glabrous. Number of ray florets per inflorescence: About 20 in a single whorl. Color: When opening, upper surface: Close to 9A. When opening, lower surface: Close to 1A. Fully opened, upper surface: Close to 15B. Fully opened, lower surface: Close to 12B; color becoming closer to 15B with development.

*Disc florets.*—Shape: Tubular; apex, five-pointed. Length: About 5 mm. Diameter: About 1 mm. Number of disc florets per inflorescence: About 80. Color: Immature: Close to 199A. Mature: Close to 166A; with development, close to N186A.

*Phyllaries.*—Quantity per inflorescence: About 18. Length: About 1.1 cm. Width: About 1.5 mm. Shape: Lanceolate. Apex: Acute. Margin: Entire. Texture: Slightly pubescent. Color, upper and lower surfaces: Close to 143A.

*Peduncles.*—Length, terminal peduncle: About 3.9 cm. Length, axillary peduncle: About 2.7 cm. Diameter: About 2 mm. Strength: Moderate. Aspect, terminal peduncle: Erect. Aspect, axillary peduncle: About 15° from vertical. Texture: Pubescent. Color: Close to 143C.

*Reproductive organs.*—Androecium: Present on disc florets only. Anther shape: Lanceolate. Anther length: About 1 mm. Anther color: Close to 185D. Pollen amount: Moderate. Pollen color: Close to 24A. Gynoecium: Present on both ray and disc florets. Pistil length: About 3 mm. Stigma shape: Two-branched. Stigma length: About 1 mm. Stigma color: Close to 183B. Style length: About 2 mm. Style color: Close to 159D.

*Seeds/fruits.*—Seed and fruit development have not been observed on plants of the new *Osteospermum*.

Disease/pest resistance: Plants of the new *Osteospermum* have not been shown to be resistant to pathogens and pests common to *Osteospermums*.

Garden performance: Plants of the new *Osteospermum* have been observed to have good garden performance and to tolerate rain, wind and temperatures ranging from about −4° C. to about 30° C.

It is claimed:

1. A new and distinct *Osteospermum* plant named 'Sunpix0805' as illustrated and described.

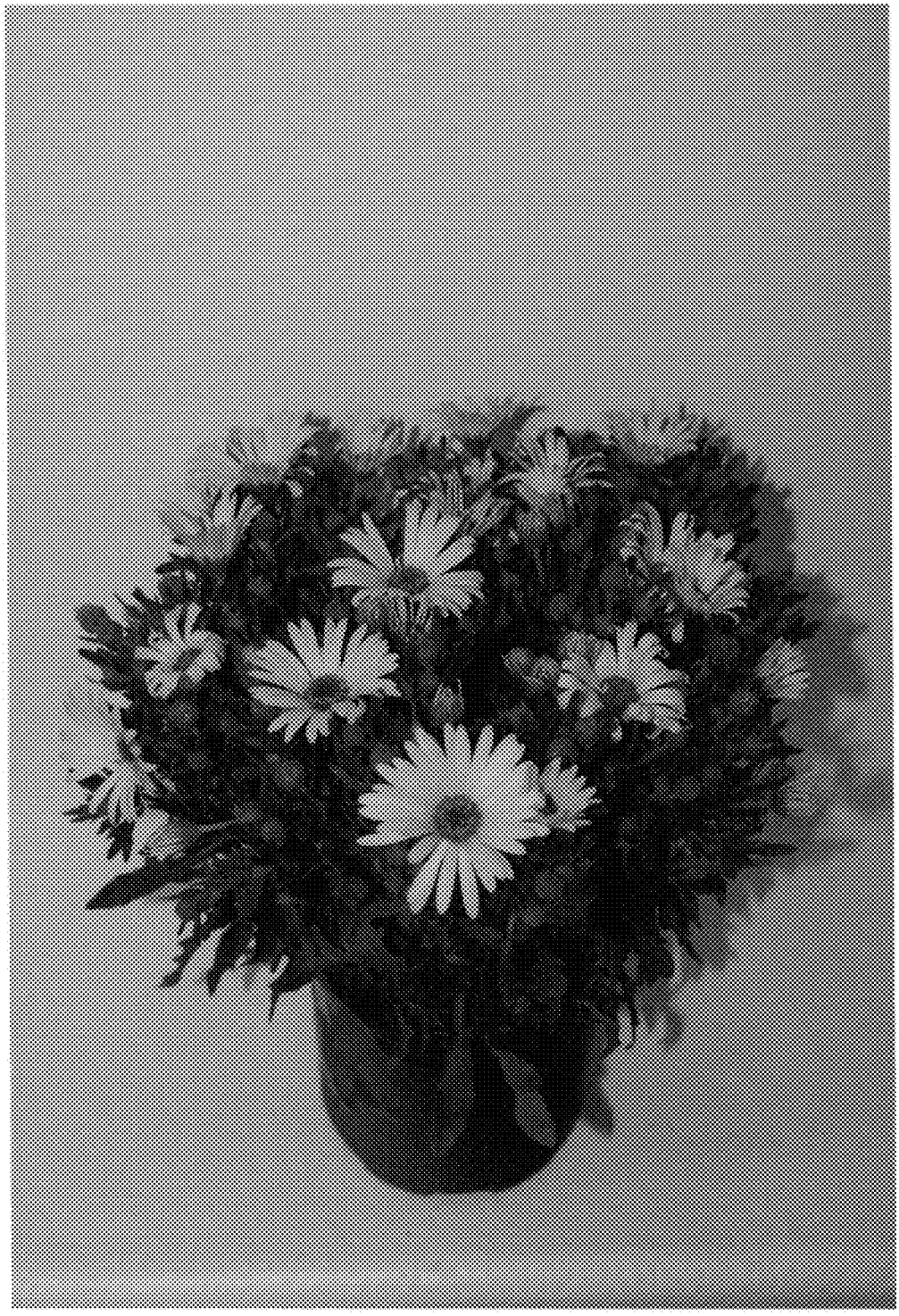

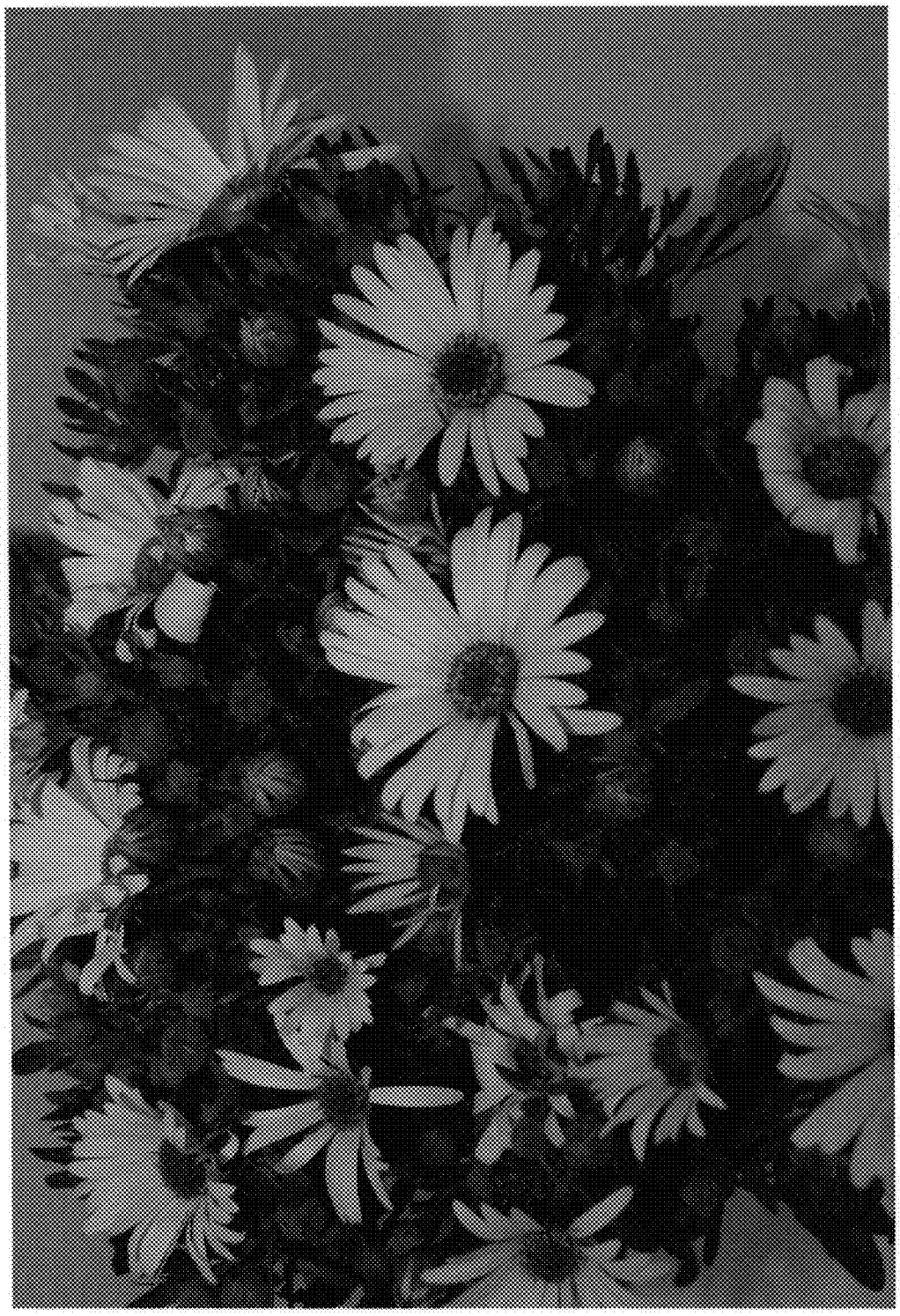

* * * * *